United States Patent
Froigneux et al.

(10) Patent No.: US 9,068,889 B2
(45) Date of Patent: Jun. 30, 2015

(54) DEVICE AND METHOD FOR OBSERVING AND FOR MEASURING RAMAN SCATTERING

(75) Inventors: Emmanuel Froigneux, Villeuneuve d'Ascq (FR); Philippe De Bettignies, Lambersart (FR)

(73) Assignee: Horiba Jobin Yvon SAS, Longjumeau (FR)

( * ) Notice: Subject to any disclaimer, the term of this patent is extended or adjusted under 35 U.S.C. 154(b) by 7 days.

(21) Appl. No.: 13/995,094

(22) PCT Filed: Dec. 20, 2011

(86) PCT No.: PCT/FR2011/053102
§ 371 (c)(1),
(2), (4) Date: Jun. 17, 2013

(87) PCT Pub. No.: WO2012/085455
PCT Pub. Date: Jun. 28, 2012

(65) Prior Publication Data
US 2013/0271760 A1 Oct. 17, 2013

(30) Foreign Application Priority Data
Dec. 21, 2010 (FR) ..................... 10 60898

(51) Int. Cl.
*G01J 3/44* (2006.01)
*G01N 21/65* (2006.01)
*G01J 3/02* (2006.01)
*G01J 3/10* (2006.01)

(52) U.S. Cl.
CPC . *G01J 3/44* (2013.01); *G01N 21/65* (2013.01); *G01J 3/02* (2013.01); *G01J 3/021* (2013.01); *G01J 3/0248* (2013.01); *G01J 3/10* (2013.01)

(58) Field of Classification Search
CPC ...... G01J 3/0248; G01J 3/0208; G01J 3/0237
USPC ........................................ 356/301
See application file for complete search history.

(56) References Cited

U.S. PATENT DOCUMENTS

| 7,561,326 B2 * | 7/2009 | Funk et al. ............... 359/368 |
| 2009/0135417 A1 * | 5/2009 | Carron et al. ............ 356/301 |
| 2010/0033811 A1 * | 2/2010 | Westphal et al. ......... 359/368 |
| 2013/0169959 A1 * | 7/2013 | Guenther ................. 356/301 |

* cited by examiner

*Primary Examiner* — Kara E Geisel
*Assistant Examiner* — Maurice Smith
(74) *Attorney, Agent, or Firm* — Brooks Kushman P.C.

(57) ABSTRACT

The present invention relates to a method and optical device for Raman spectroscopy and for observing a sample, said device including an optical means for superimposing an excitation laser beam having a spectral band $B_0$ and an observation beam having a spectral band $B_V$ so as to form a combined excitation and observation incident beam, and an optical separation means arranged in the path of a collected beam coming from scattering on the sample and including a first filtering means, a second filtering means capable of spatially separating said collected beam into a first secondary beam and two tertiary beams, each of which includes a spectral band selected from the spectral band $B_0$ of the laser, the spectral band $B_V$ of the observation beam, and the spectral band $B_R$ of the Raman scattering beam, respectively.

20 Claims, 10 Drawing Sheets

DEVICE AND METHOD FOR OBSERVING AND FOR MEASURING RAMAN SCATTERING

CROSS REFERENCE TO RELATED APPLICATIONS

This application is the U.S. national phase of PCT/FR2011/053102 filed Dec. 20, 2011, which claims priority to French Application No. 1060898 filed Dec. 21, 2010, the disclosures of which are hereby incorporated by reference in their entirety.

The present invention relates to the field of Raman spectrometry. More precisely, the invention relates to viewing device and method for a Raman spectrometer.

Since the arrival of laser sources, the Raman spectroscopy has known a rapid expansion and finds today applications in very various fields, going from fundamental research to industrial applications of process control.

The Raman spectroscopy is based on the measurement of transitions between vibrational states of a polyatomic, molecular or ionic structure (and on the rotation states in the case of gas), whatever the physical state of the sample (gas, liquid, amorphous or crystalline solid). A sample illuminated by a monochromatic light source (a laser) scatters a light that is no longer monochromatic but has scattering bands at various frequencies. Therefore, the spectrum obtained is composed of three scattering sources: the Rayleigh (elastic scattering), Stokes and anti-Stokes (inelastic scattering) bands.

The Raman frequencies are specific for each sample and are independent of the laser frequency. The Raman spectroscopy thus allows a non-destructive chemical analysis of solids, liquids, powders or gas.

More recently, the miniaturization of the optical components has made it possible to couple the Raman spectrometry with the standard optical microscopy to allow the analysis of samples with a micrometric spatial resolution. The excitation laser beam is generally focused by an objective or an optical lens. Various Raman spectrometry apparatuses have a viewing system that allows illuminating the sample and forming an image of the sample on a screen. A viewing system is generally based on the use of a white light source (conventional lamp), a viewing camera and a retractable optical component, such as a semi-transparent plate, on the optical path of the measuring instrument. The arrangement of the viewing device allows performing the focusing on the sample before the measurement, for example thanks to an autofocus system. In such a device, to perform a measurement of the sample by Raman spectrometry, the illumination and viewing device must be removed from the optical path, for example by retracting the semi-transparent plate out of the optical path. However, such a device may be difficult to handle. Indeed, the use of a retractable optical component implies a mechanical movement that generates a risk of motion blur. Moreover, the non-reproducibility of the optomechanical movement may lead to a different focus on the sample when viewed by the viewing system and by the Raman measuring system.

In certain applications, it is desirable to perform a monitoring of the sample as a function of time and it proves useful that the sample can be viewed during a series of Raman measurements. In certain particular applications, it may even be necessary to do or adjust the focus on the sample simultaneously with the measurement. However, the use of an illumination device during the Raman measurement might disturb the measurement of the Raman signals. Firstly, the excitation laser is likely to generate spurious light toward the viewing camera, which might saturate the sensor of the camera and prevent a correct viewing of the sample. Moreover, the permanent presence of an additional optical component, such as a semi-transparent plate, on the optical path, necessarily leads to a reduction of the detected Raman signal. Finally, the illumination source is likely to generate spurious scattered light not only on the sample but also on the internal components of the apparatus and thus to disturb the measurement of the Raman signals. Moreover, the difficulty to measure Raman signals comes essentially from the very low intensity of the Raman scattering compared to the intensity of the Rayleigh scattering. It is hence not possible, with the current systems, to perform simultaneously a Raman measurement and the viewing of a sample.

One of the objects of the invention is to provide viewing and Raman spectrometry device and method.

One object of the invention is to provide a device and a method for simultaneously viewing a sample and measuring the latter by Raman spectrometry. The present invention aims at remedying these drawbacks and more particularly relates to an optical device for Raman spectrometry and for viewing a sample, said device comprising:

optical superimposition means adapted to be placed on the optical path of an excitation laser beam having a spectral band $B_0$ centered about a wavelength $\lambda_0$ and on the optical path of a viewing beam having a spectral band $B_V$, distinct from the spectral band $B_0$ of the laser and distinct from the spectral band $B_R$ of the Raman scattering beam to be measured, so as to form a combined excitation and viewing incident beam toward the sample;

optical separation means adapted to be placed on the path of a collected beam coming from the scattering of the combined excitation and viewing incident beam on the sample, said optical separation means comprising:

i. a first filtering means adapted to spatially separate said collected beam into a first and a second secondary beams, said first secondary beam comprising a spectral band chosen from the spectral band $B_0$ of the laser, the spectral band $B_V$ of the viewing beam and the spectral band $B_R$ of the Raman scattering beam, and said second secondary beam comprising the two other remaining spectral bands among the spectral band $B_0$ of the laser, the spectral band $B_V$ of the viewing beam and the spectral band $B_R$ of the Raman scattering beam;

ii. a second filtering means placed on the path of the second secondary beam and adapted to spatially separate said second secondary beam into a first and a second tertiary beams, each respectively comprising one of the two remaining spectral bands among the spectral band $B_0$ of the laser, the spectral band $B_V$ of the viewing beam and the spectral band $B_R$ of the Raman scattering beam.

According to a particular embodiment of the invention, said optical superimposition means are merged with said first filtering means.

According to another particular embodiment of the invention, said optical superimposition means are merged with said second filtering means. According to various particular aspects of the invention, said optical superimposition means comprise:

an optical filter adapted to reflect said excitation laser beam of spectral band $B_0$ and to transmit said viewing beam of spectral band $B_V$;

an optical filter adapted to transmit said excitation laser beam of spectral band $B_0$ and to reflect said viewing beam of spectral band $B_V$;

said first filtering means comprises an optical filter adapted to reflect said first secondary beam and to transmit said second secondary beam;

said first filtering means comprises an optical filter adapted to transmit said first secondary beam and to reflect said second secondary beam;

said second filtering means comprises an optical filter adapted to reflect said first tertiary beam and to transmit said second tertiary beam;

said second filtering means comprises an optical filter adapted to transmit said first tertiary beam and to reflect said second tertiary beam;

said optical filter is chosen among a high-pass, low-pass, band-pass or notch filter;

the spectral band $B_0$ of the laser, the spectral band $B_V$ of the viewing beam and the spectral band $B_R$ of the Stokes lines of the Raman scattering beam are defined in wavelength in such a manner that:

$$B_V < B_0 < B_R$$

the spectral band $B_0$ of the laser, the spectral band $B_V$ of the viewing beam and the spectral band $B_R$ of the Stokes lines of the Raman scattering beam are defined in wavelength in such a manner that:

$$B_0 < B_R < B_V$$

the spectral band $B_0$ of the laser, the spectral band $B_V$ of the viewing beam and the spectral band $B_R$ of the anti-Stokes lines of the Raman scattering beam are defined in wavelength in such a manner that:

$$B_V < B_R < B_0$$

the spectral band $B_0$ of the laser, the spectral band $B_V$ of the viewing beam and the spectral band $B_R$ of the anti-Stokes lines of the Raman scattering beam are defined in wavelength in such a manner that:

$$B_R < B_0 < B.$$

According to a preferred embodiment, the device of the invention further comprises at least one excitation laser source adapted to generate an excitation laser beam having a spectral band $B_0$ centered about a wavelength $\lambda_0$, a viewing light source adapted to generate a viewing beam having spectral band $B_V$ distinct from the spectral band $B_0$ of the laser, viewing means adapted to detect the collected beam in the spectral band $B_V$, detection means adapted to detect the Raman scattering beam in the spectral band $B_R$, and an optical system adapted to direct the combined excitation and viewing incident beam toward the sample; an optical system adapted to direct the secondary or tertiary beam of spectral band $B_V$ toward said viewing means; and an optical system adapted to direct the secondary or tertiary Raman scattering beam in the spectral band $B_R$ toward said detection means.

According to still another embodiment of the invention, said excitation laser beam comprises at least one second spectral band $B'_0$ centered about a wavelength $\lambda'_0$, the excitation spectral bands $B_0$ and $B'_0$ being distinct from said viewing spectral band $B_V$ (2), said excitation beam being adapted to generate a Raman scattering beam comprising a Raman scattering spectral band $B_R$ and a Raman scattering spectral band $B'_R$, said bands $B_R$ and $B'_R$ being distinct from the excitation spectral bands $B_0$ and $B'_0$ and from the viewing spectral band $B_V$, respectively; and said device comprises optical filtering means adapted to split said collected beam so as to spatially separate said collected beam into a plurality of derived beam comprising a first derived beam comprising the spectral band $B_V$ of said viewing beam, at least one second derived collected beam comprising the Raman scattering spectral band $B_R$ and/or the Raman scattering spectral band $B'_R$, at least one third derived collected beam comprising the spectral band $B_0$ and/or the spectral band $B'_0$ of the laser excitation beam.

According to particular aspects, the device of the invention further comprises:

autofocus adjustment means, and/or image stabilization means coupled to means for relative displacement of the object with respect to the laser excitation beam.

The invention also relates to a method for Raman spectrometry and for viewing a sample comprising the following steps:

superimposing an excitation laser beam having a spectral band $B_0$ centered about a wavelength $\lambda_0$ and a viewing beam having a spectral band $B_V$ distinct from $\lambda_0$ and distinct from the spectral band $B_R$ of the Raman beam to be measured, so as to direct on a sample a combined excitation and illumination beam;

collecting an optical beam scattered by said sample;

spatially and spectrally separating said collected beam into two secondary beams, the first secondary beam comprising a spectral band chosen among the spectral band $B_0$ of the laser, the spectral band $B_V$ of the viewing beam and the spectral band $B_R$ of the Raman scattering beam, and the second secondary beam comprising the two other remaining spectral bands among the spectral band $B_0$ of the laser, the spectral band $B_V$ of the viewing beam and the spectral band $B_R$ of the Raman scattering beam, spatially and spectrally separating said second secondary beam into two tertiary beams, each comprising one of the two remaining spectral bands among the spectral band $B_0$ of the laser, the spectral band $B_V$ of the viewing beam and the spectral band $B_R$ of the Raman scattering beam;

detecting the secondary or tertiary collected beam comprising the spectral band $B_R$ of the Raman scattering beam;

detecting the secondary or tertiary collected beam comprising the spectral band $B_V$ of the viewing beam.

The invention will find a particularly advantageous application in the Raman spectrometry apparatuses.

The present invention also relates to the characteristics that will become evident from the following description and that will have to be considered either alone or in any technically possible combination thereof.

This description, which is given by way of non-limitative example, will allow a better understanding of how the invention can be implemented, with reference to the appended drawings in which:

FIG. 1 schematically shows a spectral distribution of the intensity of the excitation laser beam, the illumination and viewing beam and the Raman scattering beam;

FIG. 2 schematically shows an illustrative implementation of a device of the invention illustrating the optical path of the different incident and scattered beams;

FIG. 3 shows a device according to a preferred embodiment of the invention;

FIG. 4 schematically shows the intensity spectra of the components used in the device of FIG. 3;

The invention proposes a filter arrangement for making Raman and for viewing the sample without mobile parts and possibly simultaneously.

The idea is to use a specific spectral range for the illumination and the viewing of the sample, this spectral range being disjoint from that of the laser and of the induced Raman range.

Figure 1:
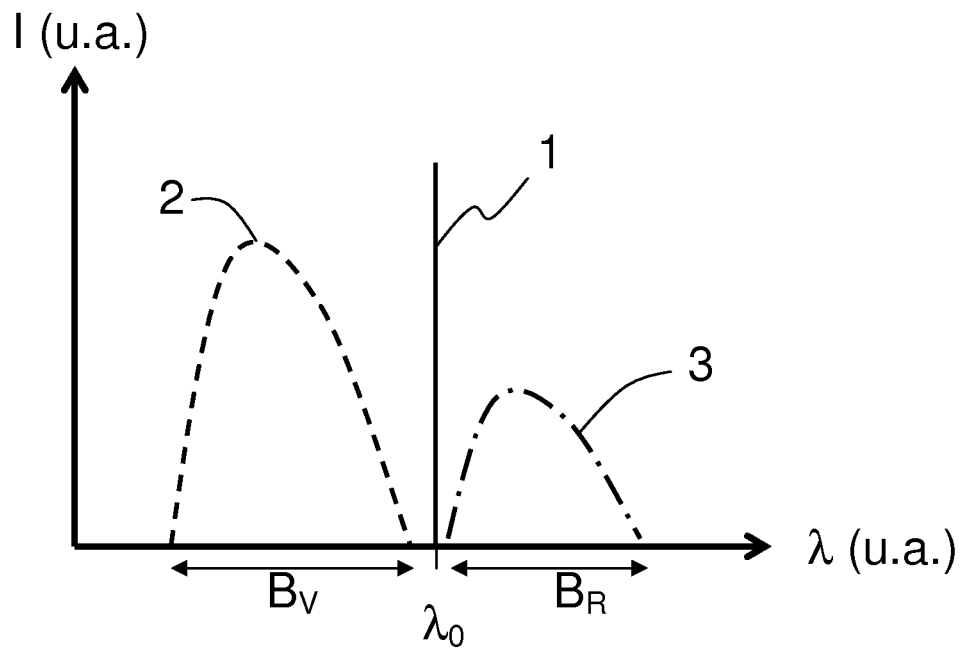

FIG. 1 very schematically shows the spectral distribution of the intensity of various measurement and viewing beams. The excitation laser beam has a wavelength $\lambda_0$ and a spectral band $B_0$ centered on the wavelength $\lambda_0$, the spectral band $B_0$ being very narrow. The excitation beam (1) generates through Raman scattering, on a sample, a Raman scattering beam whose lines are located in a spectral band $B_R$ schematically shown by the curve (3) in FIG. 1.

An aspect of the invention consists in using a viewing beam having a spectral band $B_V$ distinct from the spectral band $B_0$ of the laser and of the spectral band $B_R$ that is to be measured.

Figure 2:
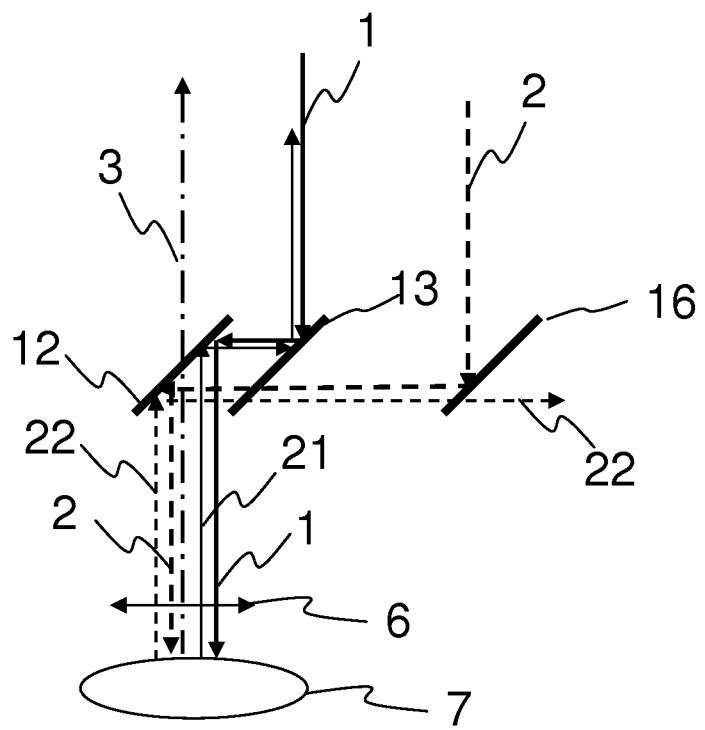

FIG. 2 schematically shows an illustrative implementation of a device according to an embodiment of the invention to illustrate the path of the various beams. The device of FIG. 2 allows superimposing an incident laser beam with an incident illumination beam and to simultaneously separate the beam scattered by the sample (7) and collected by the objective (6) as a function of its various spectral components, more precisely as a function of the spectral bands $B_0$, $B_V$ and $B_R$. The beam (21) is a backscattering beam of the excitation laser having a spectral band $B_0$ (Rayleigh scattering). The beam (3) is the Raman scattering beam, which has a spectral component $B_R$. The viewing beam (22) is a Rayleigh backscattering beam of the illumination beam (2), which has a spectral component $B_V$. The filter (12) transmits the Raman scattering beam (3) and reflects the Rayleigh scattering beams (21) and (22). The filter (13) transmits the viewing beam (22) scattered by the sample (7) and reflects the Rayleigh scattering beam at the wavelength of the laser. A separating plate (16) transmits the viewing beam (22) scattered by the sample, for example toward a viewing camera (not shown). The Raman beam (3) may be transmitted toward a Raman spectrometer so as to provide the measurement of the Raman lines in the spectral band $B_R$. The device of FIG. 2 thus allows viewing the sample thanks to the viewing beam (22) and to simultaneously perform a Raman measurement thanks to the Raman scattering beam (3), which is separated from the Rayleigh scatterings of the laser beam and of the illumination beam.

Figure 3:
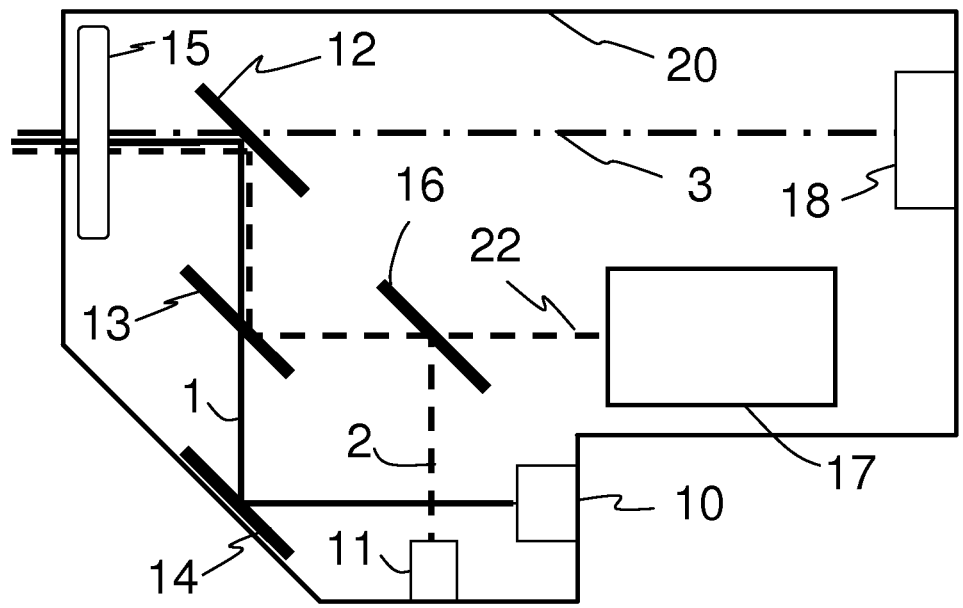

FIG. 3 shows a device according to a preferred embodiment of the invention. The device of FIG. 3 may be coupled directly to a Raman spectrometer or offset with respect to the Raman spectrometer to be placed the nearest to the sample, the device being then connected to a Raman spectrometer by optical fibers. The casing (20) comprises an entry (10) to couple an excitation laser beam and to direct it toward a first reflecting mirror (14). The laser beam (1) is transmitted by the filter (13), and reflected by the filter (12) to be transmitted toward the sample through the optical focusing component (15). The casing (20) comprises a viewing source (11) that is, for example, a green LED emitting in a wavelength range comprised between 500 and 550 nm. The viewing source (11) generates a viewing beam (2) that is directed toward a separating plate (16), and transmitted toward the filter (13). The filter (13) reflects the beam (2) toward the filter (12) that reflects also the viewing beam (2) toward the sample, so as to superimpose it to the excitation laser beam (1). The scattering beam collected through the window (15) comprises a Raman scattering beam (3) that is transmitted by the filter (12) toward a module (18) that may be either a Raman spectrometer or a fiber connector so as to transmit the Raman beam (3) toward an offset Raman spectrometer. The beam scattered by the sample at the wavelength $\lambda_0$ of the laser is reflected by the filter (12), transmitted by the filter (13) and redirected toward the entry/exit (10). The collected beam also comprises a component in the spectral band $B_V$ of the viewing source. The viewing backscattered beam (22) is reflected by the filter (12) and by the filter (13), and transmitted by the separating plate (16). This viewing beam (22) is directed by a viewing camera (17).

A prototype of offset fiber probe, based on the diagram of FIG. 3, has been made for an excitation laser having a wavelength $\lambda_0$ of 660 nm, but this principle may apply to any apparatus. The filter (12) reflects the laser (660 nm), the low-wavelength illumination (lower than 660 nm) and the light reflected by the sample. The filter (12) transmits the Raman scattering beam for wavelengths from 665 nm, the Raman range extending, in wavenumber, between 400 and 3500 cm$^{-1}$. The filter (13) transmits the excitation laser at 660 nm and reflects the illumination beam at low wavelength. The separating plate (16) allows separating the illumination beam (2) that goes from the illumination source to the sample from the viewing beam (22) that goes from the sample to a viewing camera. The device of FIG. 3 is compatible with a confocal video system. The excitation laser is coupled to the entry connector (10) via an optical fiber of core diameter 5-6 micrometers. The probe is connected to a Raman spectrometer via an optical fiber having a core diameter of about 100 micrometers. The illumination source is a green LED of aperture 15° and whose light intensity is about 6800 mcd.

Figure 4:
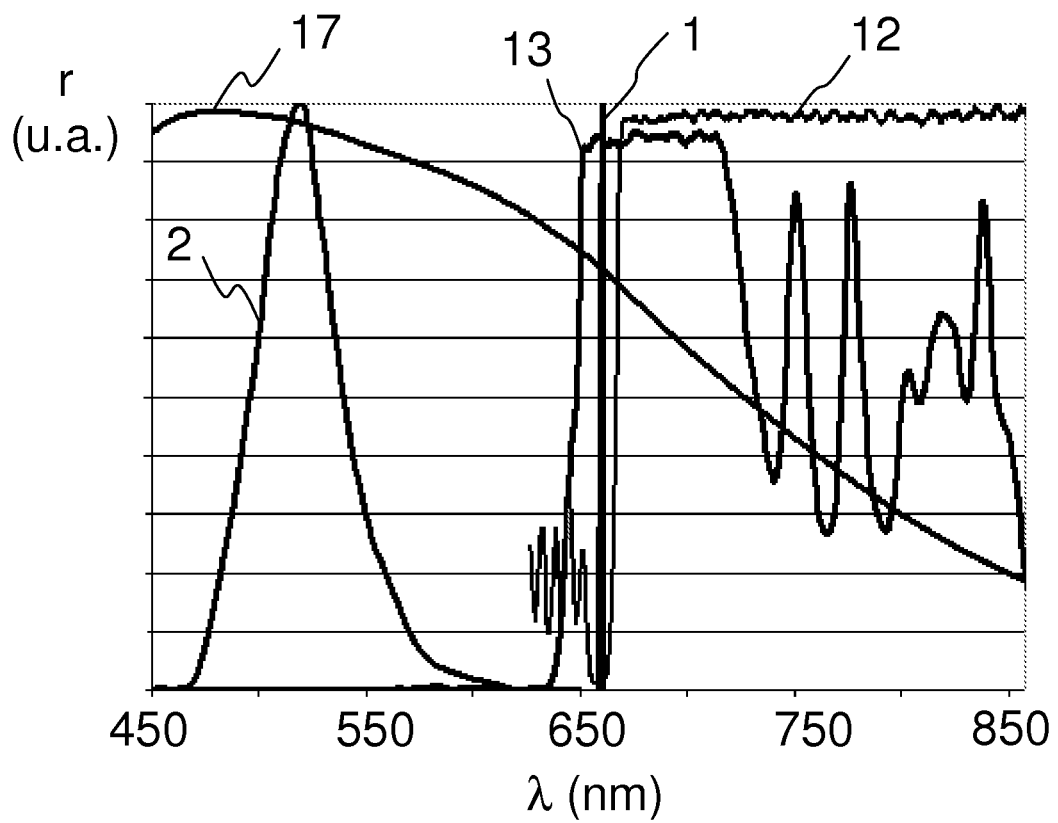

FIG. 4 schematically shows the relative spectral response of the different sources and the filters used. The laser beam (1) has a wavelength $\lambda_0$ and a very narrow spectral band $B_0$. Reference is made to the curve (2) corresponding to the spectral curve of emission of the viewing source (11). The spectral detection curve of the viewing camera (17) has a very wide spectrum with a maximum sensitivity about the spectral band $B_V$ of the viewing source. The filter (12) is a high-pass filter having a cut-off wavelength just above the wavelength $\lambda_0$ of the laser, whereas the filter (13) lets through wavelength of the laser and reflects the wavelengths of the viewing spectral band $B_V$.

FIGS. 1 to 4 describe the principle of the invention in relation with a particular embodiment of the invention. However, many variants based on the same principle are valid and will be developed in the detailed examples of FIGS. 5 to 28, as a function of the respective positions of the different spectral bands of viewing $B_V$, of laser excitation $B_0$ and of Raman scattering $B_R$.

Figure 5:
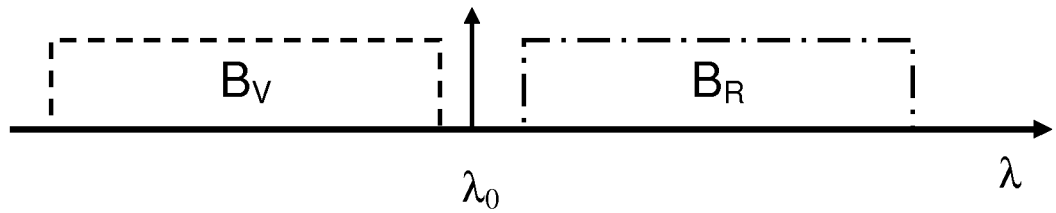
FIG. 5 shows a first case of distribution of the spectral bands.

FIG. 5 schematically shows a first case according to which the excitation wavelength $\lambda_0$ defines the spectral band $B_0$. It is searched to measure Raman scattering lines in the spectral band $B_R$ corresponding to the Stokes lines, i.e. having wavelengths higher than the excitation wavelength $\lambda_0$ of the laser. The viewing spectral band $B_V$ is located at wavelengths lower than the excitation wavelength $\lambda_0$. For example, the laser may have a wavelength of 660 nm and the viewing may be performed in the blue-green-yellow domain of the visible spectrum.

In FIGS. 6 to 9, the excitation laser beam (1) has been shown in full line and the Stokes Raman scattering beam (3) has been shown in dash-dot line. In the following of the document, the illumination beam incident on the sample and the viewing beam scattered by the sample, which are superimposed on the round trip path up to a not-shown separating plate (16), have been shown by a common dash line (2).

Figure 6:
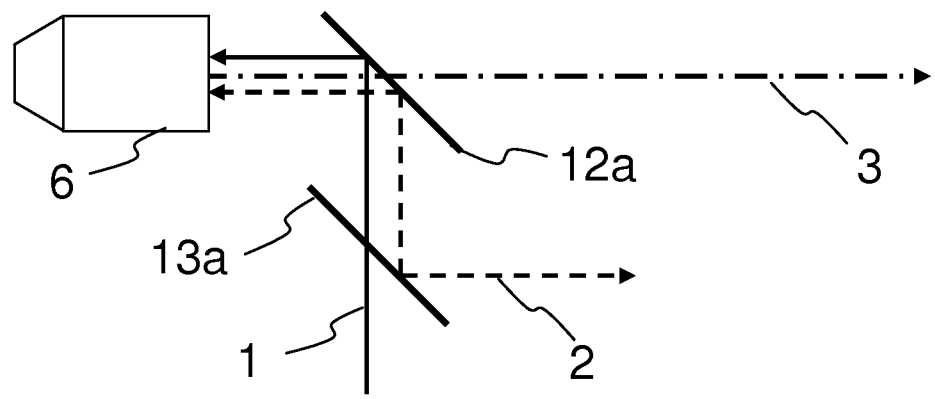
FIGS. 6 to 9 show various embodiments using the spectral band distribution of FIG. 5.

FIG. 6 shows a first embodiment using the distribution of the spectral bands of FIG. 5. The laser excitation beam (1) is transmitted by a filter (13a), and reflected by a filter (12a) toward a focusing objective (6). The viewing beam (2) is reflected by the filter (13a), then by the filter (12a) toward the objective (6). The collected beam comprises the Raman scattering beam (3) that is transmitted by the filter (12a). The collected scattered beam also comprises a viewing beam that is reflected by the filter (12a), then by the filter (13a). The filter (13a) is a high-pass or band-pass filter having a cut-off wavelength located between the viewing band $B_V$ and the band $B_0$ of the laser. The filter (12a) is a high-pass filter having a cut-off wavelength located between the wavelength $\lambda_0$ of the laser and the band $B_R$ of the Raman scattering. Thus, the filter (13a) serves to superimpose the laser excitation beam and the illumination beam toward the sample and on the scattering beam to separate the viewing beam from the back-scattering at the wavelength of the laser. The filter (12a) serves to separate on the one hand the beam of the Raman scattering (3) and on the other hand the spectral components of the scattering beam in the spectral band $B_0$ of the laser and the spectral band $B_V$ of the viewing beam.

Figure 7:
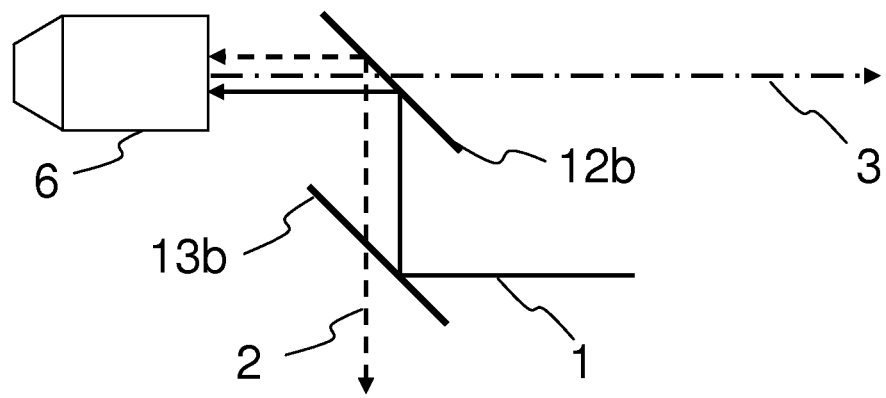

FIG. 7 shows a second embodiment of a device according to the invention, still using the spectral distribution according to the diagram of FIG. 5. Unlike in FIG. 6, the laser beam (1) is first reflected by a filter (13b) before being reflected on a filter (12b). Symmetrically, the illumination beam (2) is transmitted by the filter (13b) before being reflected by the filter (12b). The scattered and collected beam is directed toward the first filter (12b) that transmits the Raman scattering beam (3) and reflects the components of the scattered beam in the spectral band $B_0$ of the laser and in the spectral band $B_V$ of the viewing beam 2. The filter (13b) separates the scattered viewing beam from the beam scattered at the wavelength of the laser. As in FIG. 6, the filter (12b) is a high-pass filter having a cut-off wavelength between the wavelength $\lambda_0$ of the laser and the Raman spectral band $B_R$. The filter (13b) is a low-pass or notch filter having a cut-off wavelength located between the viewing spectral band $B_V$ and the spectral band $B_0$ that transmits the beam in the spectral band $B_V$ and reflects a beam having wavelengths in the spectral band $B_0$.

Figure 8:
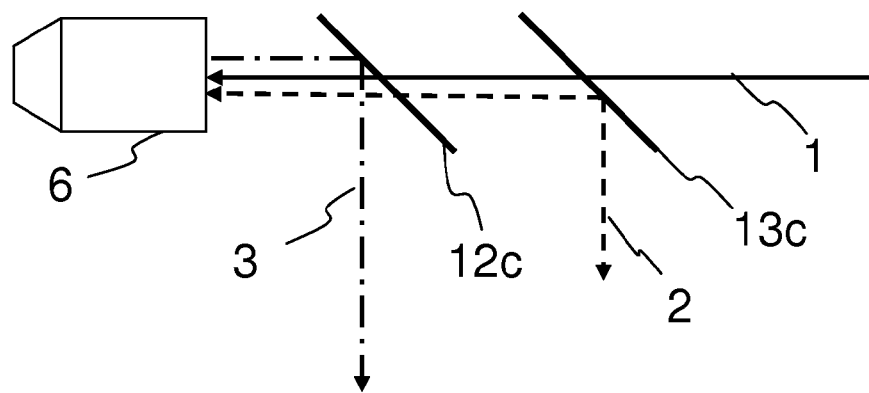

FIG. 8 schematically shows a third embodiment based on the spectral distribution of the diagram of FIG. 5. The excitation laser beam (1) is transmitted by a filter (13c), then by a filter (12c) toward the objective (6). The illumination beam (2) is reflected on the filter (13c) and transmitted by the filter (12c). The Raman scattering beam (3) is reflected by the filter (12c). The scattering beam (2) in the viewing spectral band $B_V$ is transmitted by the filter (12c) and reflected by the filter (13c). The filter (13c) is a high-pass or band-pass filter having a cut-off wavelength located between the spectral band $B_V$ and the band $B_0$ that transmits the band $B_0$ and reflects the band $B_V$. The filter (12c) is a low-pass filter having a cut-off wavelength comprised between the band $B_0$ and the Raman band $B_R$ that transmits the wavelength of the spectral band $B_V$ and the spectral band $B_0$ and reflects a beam having wavelengths in the spectral band $B_R$.

Figure 9:
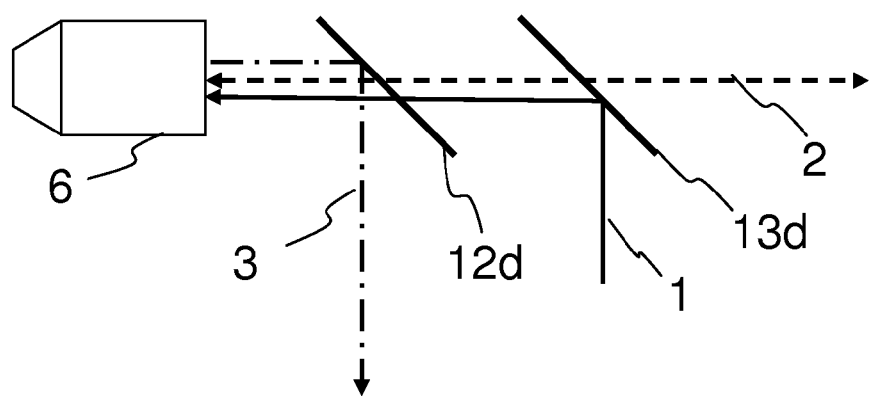

FIG. 9 shows a fourth embodiment according to the spectral distribution of the diagram of FIG. 5. The device comprises a filter (12d), a filter (13d) and an objective (6). The excitation laser beam (1) is reflected on the filter (13d), and transmitted by the filter (12d) toward the objective (6). The illumination and viewing beam (2) is transmitted by the filter (13d) and the filter (12d). The collected Raman scattering beam (3) is reflected by the filter (12d) whereas the scattering beam in the spectral band $B_V$ of the viewing beam is transmitted by the filter (12d) and by the filter (13d). The filter (13d) is a low-pass or notch filter having a cut-off wavelength located between the viewing band $B_V$ and the band $B_0$ of the laser, which transmits the viewing beam $B_V$ and reflects the band $B_0$. The filter (12d) is a low-pass filter that transmits the bands $B_0$ and $B_V$ and reflects the Raman scattering band $B_R$. The filter (12d) has a cut-off wavelength comprised between the band $B_0$ and the band $B_R$.

Figure 10:
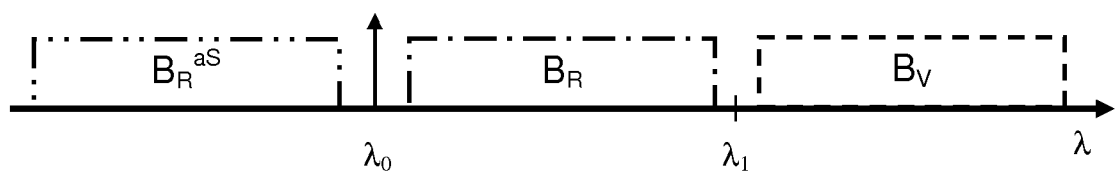
FIG. 10 shows a second case of distribution of the spectral bands.

FIG. 10 shows a second case of distribution of the spectral bands: the laser excitation spectral band, the Stokes Raman (spectral band $B_R$) and anti-Stokes Raman (spectral band $B_R^{aS}$) bands, and the viewing band $B_V$.

For example, the wavelength $\lambda_0$ of the excitation laser is located at 473 nm, whereas the viewing spectral band $B_V$ is in the yellow-red part of the visible spectrum, for example in a wavelength range above 600 nm.

The Stokes Raman band is at wavelengths higher than the laser excitation wavelength $\lambda_0$ and lower than a wavelength $\lambda_1$, itself lower than the viewing band $B_V$.

The anti-Stokes Raman scattering band is located at wavelengths lower than the laser excitation wavelength $\lambda_0$.

The configurations illustrated in FIGS. 11, 12, 13, 14, 17 and 18 allow performing either Stokes Raman measurements alone, or simultaneous Stokes and anti-Stokes Raman measurements, as described hereinafter.

Figure 11:
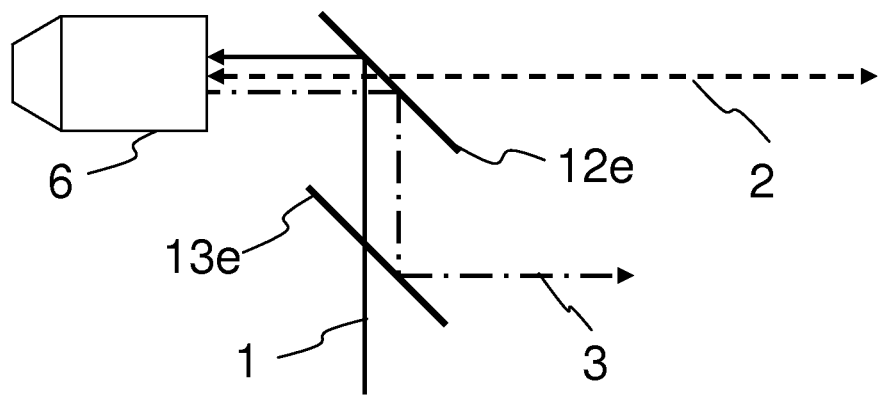
FIGS. 11 to 18 show various embodiments using the spectral band distribution of FIG. 10.

FIG. 11 shows a first embodiment according to the spectral distribution of FIG. 10.

First will be described the embodiment of FIG. 11 for measurement of the Stokes lines alone, then for measurement of the Stokes and anti-Stokes lines.

Configuration of FIG. 11 for the Stokes mode

The excitation laser beam (1) is transmitted by a filter (13e) and reflected by a filter (12e). The illumination and viewing beam (2) is transmitted by the filter (12e) that retransmits the scattered beam in the viewing band $B_V$.

The filter (12e) reflects the Raman scattering beam (3). The filter (13e) reflects the Raman scattering beam (3).

In the Stokes configuration, the filter (13e) is a low-pass filter that transmits the band $B_0$ and reflects the band $B_R$, which has thus a cut-off wavelength located between the band $B_0$ and the band $B_R$.

The filter (12e) is a high-pass filter that transmits the viewing band $B_V$ and reflects the spectral bands $B_0$ and $B_R$.

The filter (12e) is a filter having a cut-off wavelength comprised between the Raman band $B_R$ and the viewing band $B_V$.

Configuration of FIG. 11 for the Stokes and anti-Stokes mode

In the configuration of FIG. 11 where it is searched to measure both the Stokes and anti-Stokes lines, the filter (13e) is a band-pass filter that transmits the band $B_0$ and reflects the Stokes Raman bands $B_R$ and the anti-Stokes Raman band $B_R^{aS}$.

Figure 12:
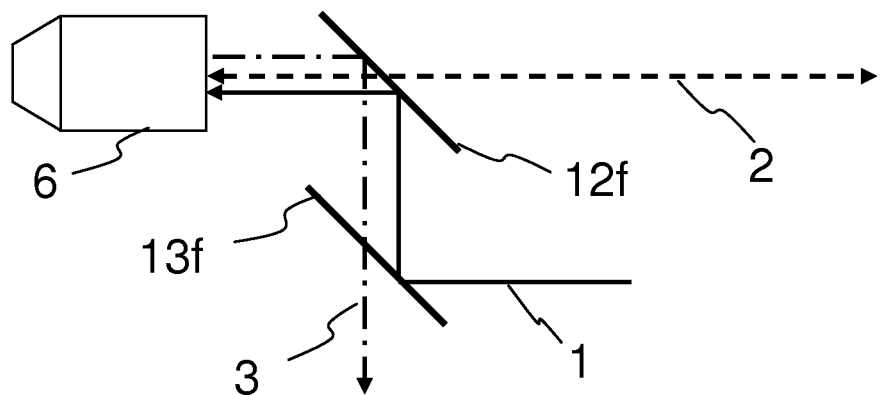

Configuration of FIG. 12

FIG. 12 schematically shows a second embodiment based on the spectral distribution of the diagram of FIG. 10. The device of FIG. 12 comprises a filter (13f) that reflects the laser excitation beam (1). The illumination and viewing beam (2) is transmitted by the filter (13f) that reflects the scattered Raman beam (3) and transmits the part of the beam scattered in the viewing band $B_V$. The filter (13f) separates the Raman beam (3) from the Rayleigh scattered beam at the laser wavelength.

The filter (12f) is a high-pass filter that transmits the viewing band $B_V$ and reflects the spectral bands $B_0$ and $B_R$ and has a cut-off wavelength located between $B_R$ and $B_V$.

The filter (13f) transmits the Raman scattering spectral band $B_R$ and reflects the laser band $B_0$. In the case where it is searched only to measure the Stokes Raman scattering band, the filter (13f) is a high-pass filter having a cut-off wavelength located between the spectral bands $B_0$ and $B_R$. In the case where it is searched to measure simultaneously the Stokes and anti-Stokes Raman scattering lines, the filter (13f) is a notch filter that reflects the spectral band $B_0$ of the excitation beam and transmits the Stokes and anti-Stokes Raman scattering bands $B_R$ and $B_R^{aS}$.

Figure 13:
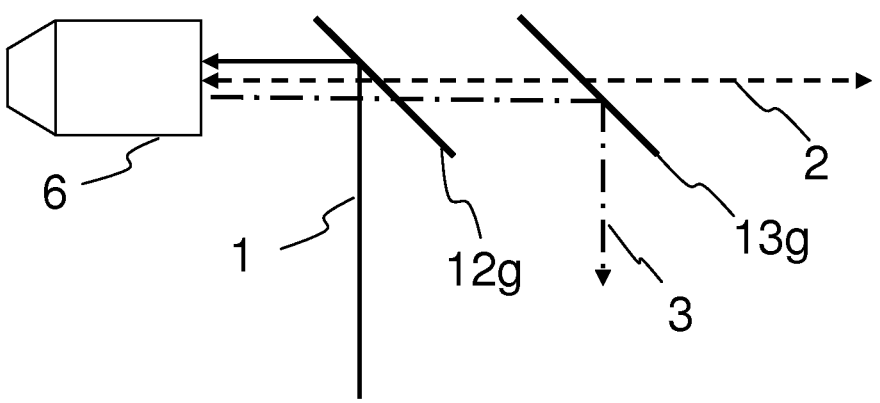

FIG. 13 shows a third embodiment according to the spectral distribution of FIG. 10.

The filter (12g) superimposes the laser excitation beam (1) and the illumination and viewing beam (2) by reflecting the laser beam (1) and transmitting the illumination and viewing beam (2) in the spectral band $B_V$. The filter (12g) transmits the viewing beam in the spectral band $B_V$ and the Raman scattering beam (3) and reflects the Rayleigh scattering beam in the spectral band $B_0$.

The filter (13g) transmits the viewing beam (2) in the spectral band $B_V$ and reflects the Raman scattering beam (3). The filter (13g) is a high-pass filter having a cut-off wavelength located between the Raman spectral band $B_R$ and the viewing band $B_V$, so as to transmit the viewing band $B_V$ and to reflect the spectral band $B_R$.

In the case where it is desired to measure only the Raman spectral band of the Stokes lines, the filter (12g) is a high-pass filter that transmits the spectral band $B_R$, the spectral band $B_V$ and reflects the spectral band $B_0$.

In the case where it is desired to measure both the Stokes and anti-Stokes lines, the filter (12g) is a notch filter that reflects the spectral band $B_0$, transmits the anti-Stokes Raman spectral band, the Stokes Raman spectral band and the viewing spectral band $B_V$.

Figure 14:
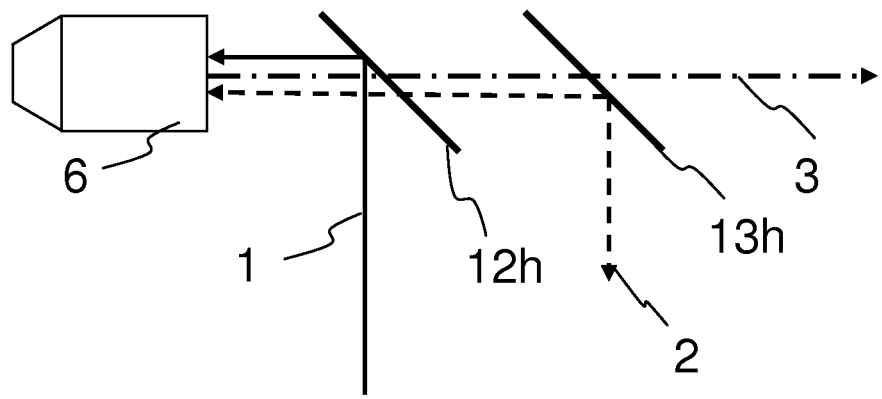

FIG. 14 shows a fourth embodiment according to the spectral distribution of FIG. 10.

The filter (12h) allows superimposing the excitation laser beam (1) and the illumination and viewing beam (2) toward the sample.

On the scattered collected beam, the filter (12h) reflects the signal scattered by Rayleigh scattering in the spectral band $B_0$, transmits the viewing beam in the spectral band $B_V$ and the Rayleigh scattering beam in the spectral band $B_R$ or $B_R^{aS}$.

The filter (13h) is a low-pass filter that transmits the Raman scattering band $B_R$ and reflects the viewing spectral band $B_V$.

In the case of measurement of only Stokes lines, the filter (12h) is a high-pass filter having a cut-off wavelength comprised between the spectral band $B_0$ and the spectral band $B_R$ so as to reflect the spectral band $B_0$ and to transmit the spectral bands $B_R$ and $B_V$.

In the case where it is desired to measure the Stokes lines and the anti-Stokes lines, the filter (12h) is a notch filter that reflects the spectral band $B_0$ and transmits the Stokes and anti-Stokes spectral bands $B_R$ and $B_R^{aS}$, as well as the lines of the viewing spectral band $B_V$.

Figure 15:
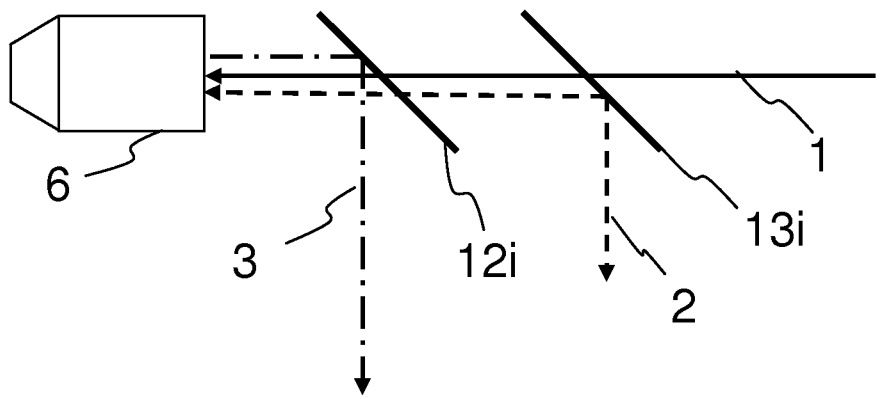

FIG. 15 shows a fifth embodiment for measurement of the Stokes Raman lines following the distribution of FIG. 10.

The filter (13i) allows superimposing the excitation laser beam (1) and the illumination and viewing beam (2) toward the object 6 and the sample.

The filter (12i) transmits both the laser excitation beam (1) and the viewing beam (2).

On the collected scattering beam, the filter (12i) separates the Raman scattering beam (3) from the viewing beam (2). The filter (13i) reflects the viewing beam (2) and transmits the Rayleigh scattered beam at the laser wavelength.

The filter (13i) is a low-pass filter that transmits the band $B_0$ and reflects the band $B_V$.

The filter (12i) is a wide notch filter that transmits the band $B_0$, reflects the Raman band $B_R$ and transmits the viewing band $B_V$.

Figure 16:
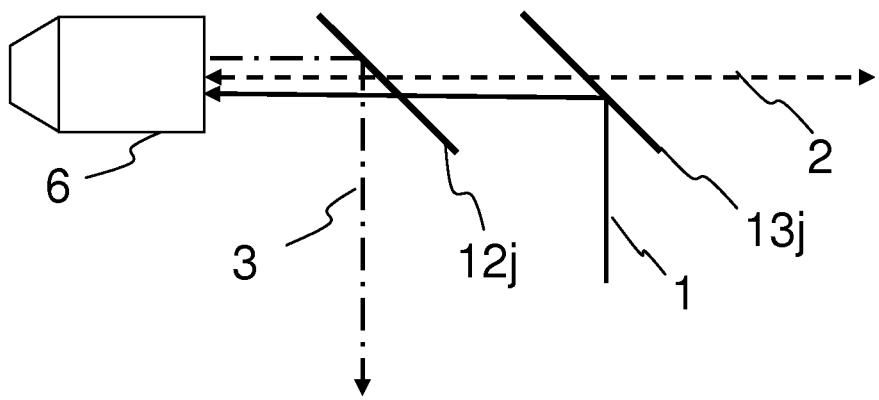

FIG. 16 shows another embodiment for measurement of the Stokes Raman lines alone, according to the spectral distribution of FIG. 10. The device of FIG. 16 comprises a filter (13j) that allows superimposing the excitation laser beam (1) and the viewing beam by reflecting the laser beam in the spectral band $B_0$ and transmitting the viewing beam in the spectral band $B_V$.

The filter 12j transmits simultaneously the excitation beam and the illumination and viewing beam (2).

The filter (12j) reflects the Raman scattering beam (3) in the spectral band $B_R$ and transmits the Rayleigh scattering beam at the laser wavelength in the spectral band $B_0$ as well as the viewing beam (2) scattered by the sample in the spectral band $B_V$.

The filter (13j) separates the viewing beam (2) in the spectral band $B_V$ from the Rayleigh scattering beam in the spectral band $B_0$.

The filter (12j) is a wide notch filter that transmits the spectral band $B_0$, reflects the Raman spectral band $B_R$ and transmits the viewing band $B_V$.

The filter (13j) is a high-pass filter having a cut-off wavelength comprised between the spectral band $B_0$ and the viewing band $B_V$.

Figure 17:
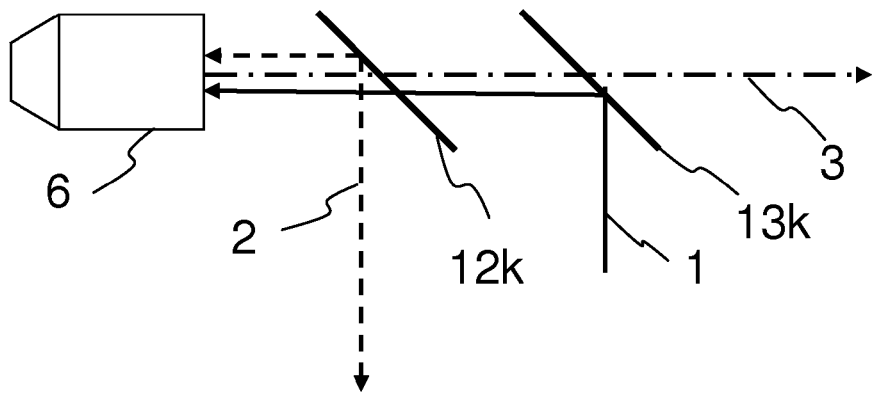

FIG. 17 shows another embodiment in relation with the spectral distribution of the diagram of FIG. 10. The device comprises a filter (12k) that allows superimposing the laser excitation beam (1) and the viewing beam (2) by transmitting the beam in the spectral band $B_0$ and reflecting the beam in the spectral band $B_V$.

The collected scattering beam comprises a spectral component in the viewing band $B_V$ that is reflected by the filter (12k). The filter (12k) is a low-pass filter that transmits the spectral band $B_0$ and the Raman scattering spectral band $B_R$ and that reflects the spectral band $B_V$.

The filter (13k) transmits the Raman scattering beam (3) in the Raman spectral band and reflects the Rayleigh scattering beam in the spectral band $B_0$. For the measurement of the Stokes lines, the filter (13k) may be a high-pass filter having a cut-off wavelength located between the spectral band $B_0$ and the Stokes Raman spectral band $B_R$. For the simultaneous measurement of the Stokes and anti-Stokes lines, the filter (13k) is a notch filter that reflects the spectral band $B_0$ and transmits the Stokes and anti-Stokes Raman scattering spectral bands $B_R$ and $B_R^{aS}$.

Figure 18:
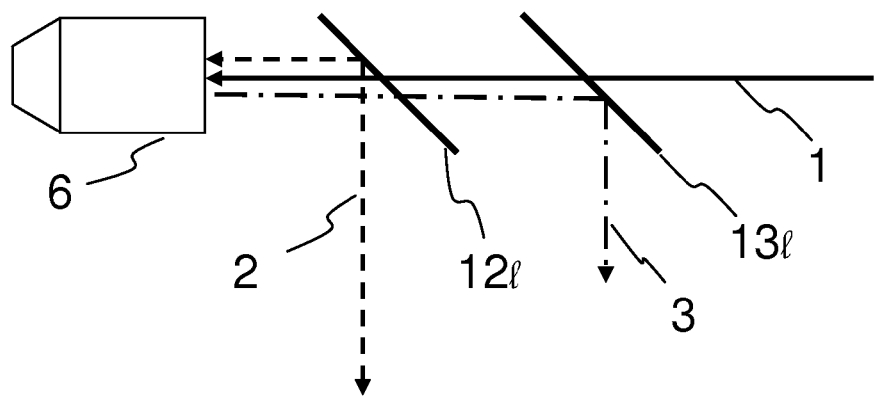

FIG. 18 shows another embodiment for a spectral distribution following the path of FIG. 10.

The device comprises a filter (12l) that allows superimposing the laser excitation beam and the viewing beam (2) by transmitting the laser excitation beam (1) and reflecting the viewing beam (2).

On the scattering beam, the filter (12l) allows extracting the viewing beam in the viewing spectral band $B_V$ and transmits the Raman scattering signal in the band $B_R$ as well as the Rayleigh scattering signal in the spectral band $B_0$. The filter (12l) is a low-pass filter that transmits the band $B_0$ and the band $B_R$ and reflects the band $B_V$, and has thus a cut-off wavelength located above the wavelength $\lambda_0$ between the Raman band $B_R$ and the viewing spectral band $B_V$.

The filter (13*l*) reflects the Raman scattering signal and transmits the Rayleigh scattering signal in the spectral band $B_0$. For the measurement of only the Stokes Raman lines, the filter (13*l*) is a low-pass filter that transmits the spectral band $B_0$ and reflects the Raman spectral band $B_R$. In the case where it is desired to measure simultaneously the Stokes and anti-Stokes Raman scattering lines, the filter (13*l*) is a band-pass filter that transmits only the spectral band $B_0$ and reflects the Stokes and anti-Stokes Raman scattering spectral bands $B_R$ and $B_R^{aS}$.

Figure 19:
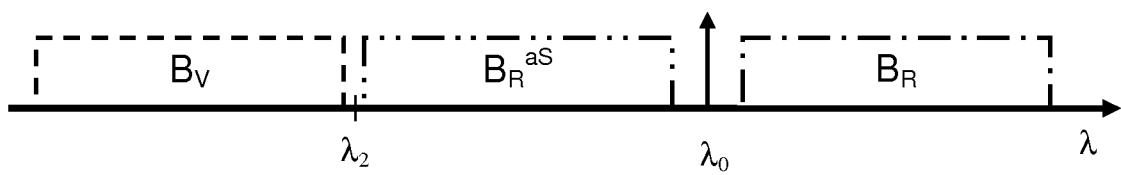
FIG. 19 shows a third case of distribution of the spectral bands.

FIG. 19 shows a third case of spectral distribution of the laser excitation viewing bands in the case where the anti-Stokes and Stokes Raman lines are measured. The viewing band $B_V$ is herein located at wavelengths lower than the anti-Stokes Raman line scattering band $B_R^{aS}$. The configuration described in relation with FIGS. 20 to 23 allows performing measurements either of Stokes Raman lines alone, or of Stokes and anti-Stokes Raman lines simultaneously.

Figure 20:
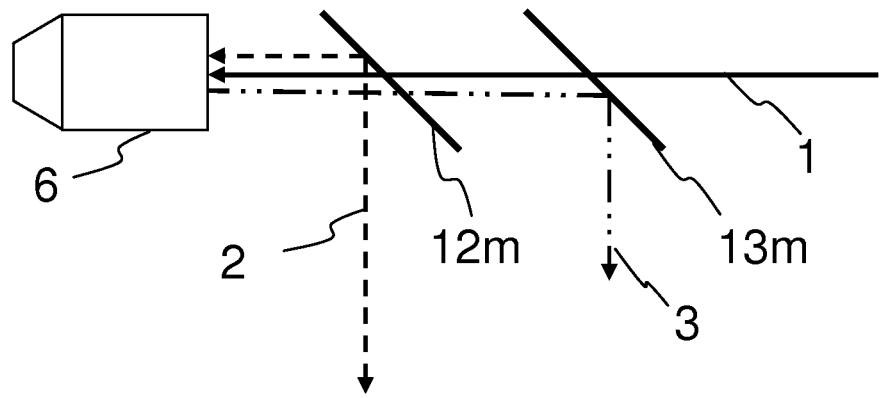
FIGS. 20 to 23 show various embodiments using the spectral band distribution of FIG. 19.

In FIG. 20, the filter (12*m*) allows superimposing the excitation laser beam (1) and the viewing beam (2). The excitation beam (1) being transmitted and the viewing beam (2) being reflected by the filter (12*m*). On the scattered beam, the filter (12*m*) allows extracting a scattered beam in the viewing band $B_V$ and transmitting the Raman scattering beam (3) as well as the Rayleigh scattering beam in the spectral band $B_0$. The filter (12*m*) is a high-pass filter having a cut-off wavelength located between the viewing band $B_V$ and the anti-Stokes Raman scattering band. The filter (12*m*) transmits the signals in the bands $B_0$, $B_R^{aS}$ and, possibly the Stokes band $B_R$, and reflects the viewing band $B_V$. In the case where it would be desired to measure only the anti-Stokes lines, the filter (13*m*) is a high-pass filter that transmits the spectral band $B_0$ and reflects the anti-Stokes Raman scattering spectral band. In the case where it is desired to measure simultaneously the Stokes and anti-Stokes lines, the filter (13*m*) is a band-pass filter that transmits the spectral band $B_0$ and reflects the Stokes and anti-Stokes Raman scattering bands.

Figure 21:
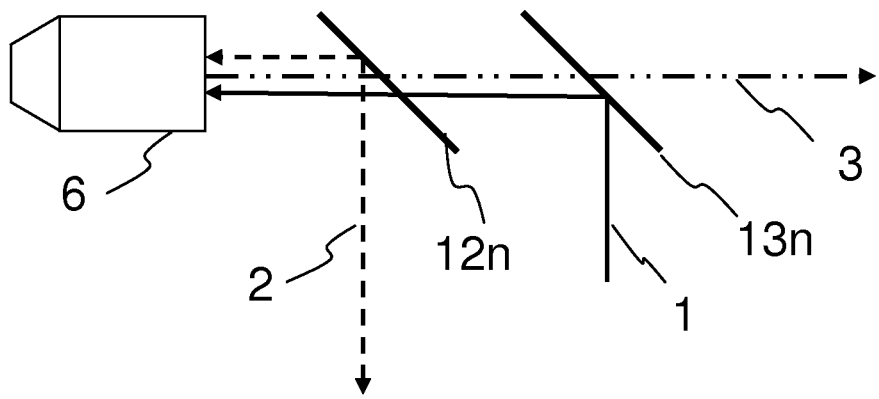
Figure 22:
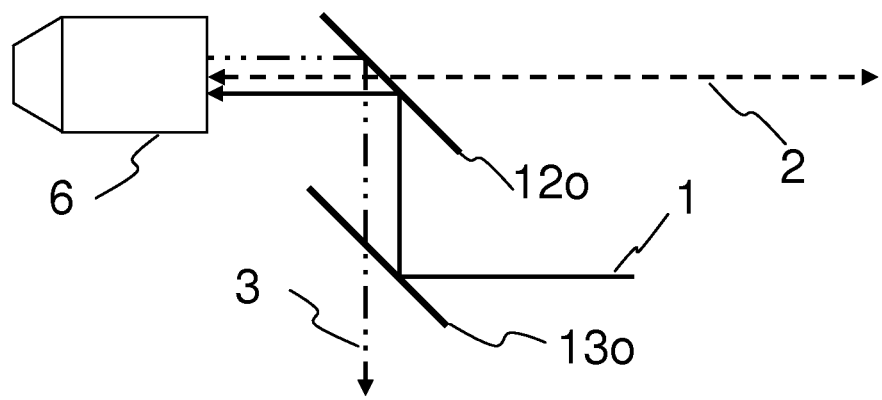

FIG. 21 shows another embodiment corresponding to the distribution schematically shown in FIG. 19. The device comprises a filter (12*n*) and a filter (13*n*). The filter (12*n*) allows superimposing the excitation laser beam (1) and the viewing beam (2) by reflecting the beam (2) and transmitting the beam (1). On the collected scattering beam, the filter (12*n*) allows extracting the scattered beam in the viewing band $B_V$ and transmitting the scattered beams in the band $B_0$ as well as in the Raman scattering band. The filter (13*n*) allows separating the scattered beam in the spectral band $B_0$ of the excitation laser from the Raman scattering beam (3). The filter (12*n*) is a high-pass filter that transmits the spectral bands $B_0$ and $B_R^{aS}$ (anti-Stokes Raman) and that reflects the viewing spectral band $B_V$. In the case where it is desired to measure only the anti-Stokes lines, the filter (13*n*) is a low-pass filter that transmits the anti-Stokes scattering band $B_R^{aS}$ and reflects the spectral band $B_0$. In the case where it is desired to measure both the Stokes and anti-Stokes Raman lines, the filter (13*n*) is a notch filter that reflects the spectral band $B_0$ and transmits the Stokes and anti-Stokes Raman scattering spectral bands $B_R$ and $B_R^{aS}$. FIG. 22 still shows another embodiment according to the diagram of FIG. 19, wherein a filter (12*o*) allows superimposing the excitation laser beam (1) and the illumination and viewing beam (2) by reflecting the laser beam (1) and transmitting the illumination and viewing beam (2) in the spectral band $B_V$. On the scattering beam, the filter (12*o*) transmits the scattered beam in the viewing band $B_V$ and reflects the scattered beam in the Raman scattering bands and in the Rayleigh scattering band $B_0$. The filter (12*o*) is a low-pass filter that transmits the viewing band $B_V$ and reflects the anti-Stokes scattering bands $B_R$, the band $B_0$ and possibly the Stokes Raman scattering band. The filter (13*o*) transmits the scattered beam in the Raman spectral bands and reflects the Rayleigh beam scattered in the laser spectral band $B_0$. In the case where it is desired to measure only the anti-Stokes band, the filter (13*o*) is a low-pass filter that transmits the anti-Stokes Raman scattering band and reflects the spectral band $B_0$. In the case where it is desired to measure simultaneously the Stokes and anti-Stokes lines, the filter (13*o*) is a notch filter that reflects the spectral band $B_0$ and transmits the Stokes and anti-Stokes Raman scattering spectral bands $B_R$ and $B_R^{aS}$.

Figure 23:
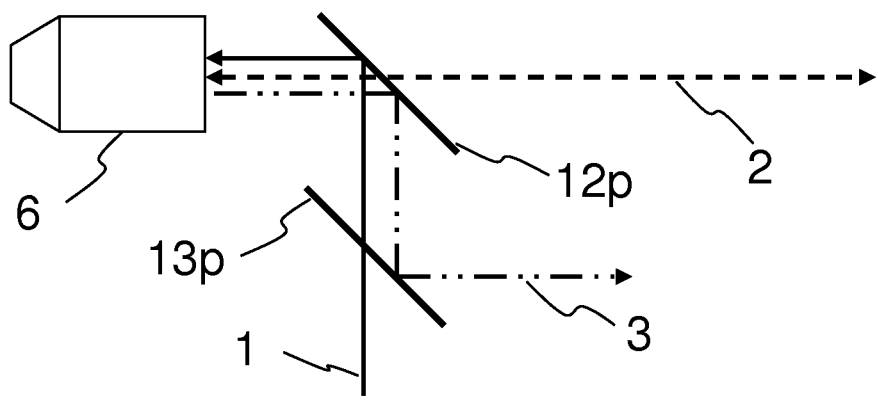

FIG. 23 describes a fourth embodiment in relation with the spectral distribution of FIG. 19. The filter (12*p*) allows superimposing the excitation laser beam (1) and the illumination and viewing beam (2) by reflecting the laser beam and transmitting the illumination and viewing beam in the spectral band $B_V$. On the collected scattered beam, the filter (12*p*) transmits the viewing beam (2) in the spectral band $B_V$ and reflects the Raman scattering signals in the spectral band $B_R$ and the beam scattered by Rayleigh scattering in the spectral band $B_0$. The filter (12*p*) thus allows extracting the viewing beam (2). The filter (13*p*) allows separating the Rayleigh scattering beam in the spectral band $B_0$ and the Raman scattering beam (3). The filter (12*p*) is a low-pass filter that transmits the viewing band $B_V$, reflects the anti-Stokes Raman scattering band and the spectral band $B_0$. In the case where it is desired to measure only the anti-Stokes lines, the filter (13*p*) is a high-pass filter that transmits the spectral band $B_0$ and reflects the anti-Stokes Raman scattering band $B_R^{aS}$. In the case where it is desired to measure simultaneously the Stokes and anti-Stokes lines, the filter (13*p*) is a band-pass filter that transmits the spectral band $B_0$ and reflects the Stokes and anti-Stokes Raman scattering spectral bands $B_R$ and $B_R^{aS}$.

Figure 24:
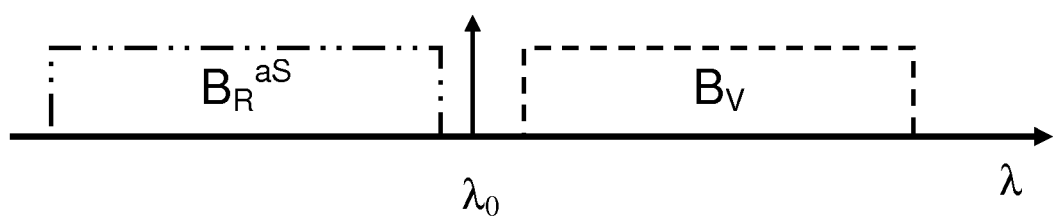
FIG. 24 shows a fourth case of distribution of the spectral bands.

FIG. 24 shows a fourth case where it is desired to measure only the scattering of the anti-Stokes Raman lines and where the viewing spectral band $B_V$ is located above the excitation laser band $B_0$. FIGS. 25 to 28 show various embodiments according to the spectral distribution of FIG. 24.

Figure 25:
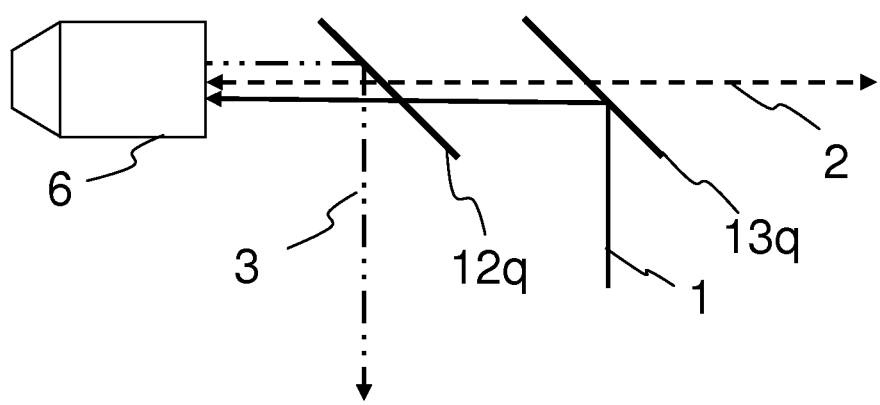
FIGS. 25 to 28 show various embodiments using the spectral band distribution of FIG. 24.

In FIG. 25, a filter (13*q*) allows superimposing the excitation beam that is reflected by the filter (13*q*) and a viewing beam (2) transmitted by this filter. On the scattering beam, a filter (12*q*) reflects the scattered beam in the anti-Stokes Raman band and transmits the scattered beam in the viewing band and in the spectral band $B_0$. The filter (13*q*) allows transmitting the scattered signal in the viewing band $B_V$ and reflecting the Rayleigh scattering beam in the spectral band $B_0$. The filter (12*q*) is a high-pass filter having a cut-off wavelength comprised between the anti-Stokes Raman spectral band $B_R^{aS}$ and the spectral band $B_0$, which thus transmits the spectral band $B_0$ and viewing band $B_V$ and reflects the anti-Stokes Raman spectral band. The filter (13*q*) is a high-pass or notch filter having a cut-off wavelength located between the viewing band and the band $B_0$ that transmits the spectral band $B_V$ and reflects the spectral band $B_0$.

Figure 26:
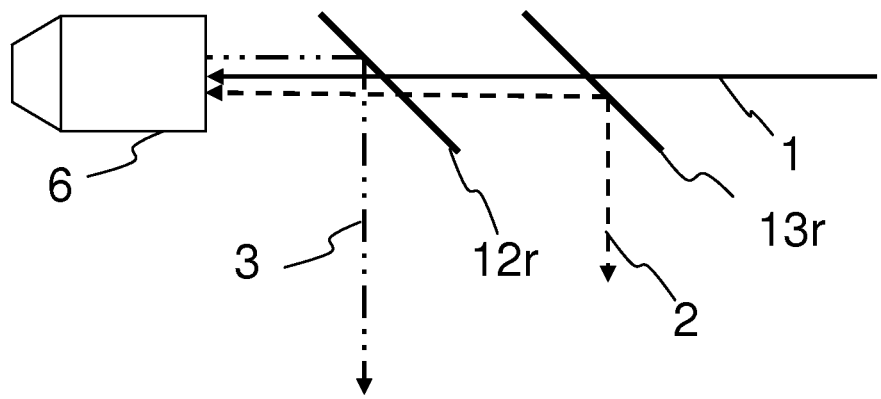

FIG. 26 describes a second embodiment in relation with the spectral distribution of FIG. 24. The filter (13*r*) allows superimposing the excitation laser beam (1) transmitted and the illumination and viewing beam (2) that is reflected by the filter (13*r*). The filter (12*r*) transmits the combined excitation and viewing beam. On the scattered beam, the filter (12*r*) reflects the anti-Stokes Raman scattering beam (3) and transmits the scattered beam in the spectral band $B_0$ and in the viewing band $B_V$. The filter (13*r*) separates the beam scattered in the viewing beam $B_V$ from the beam scattered in the band $B_0$. The filter (12r) is a high-pass filter having a cut-off wavelength comprised between the anti-Stokes Raman scattering band and the band $B_0$. The filter (12r) thus reflects the anti-Stokes Raman band and transmits the spectral bands $B_0$ and $B_V$. The filter (13r) is a low-pass or band-pass filter that transmits the spectral band $B_0$ and reflects the viewing band $B_V$.

Figure 27:
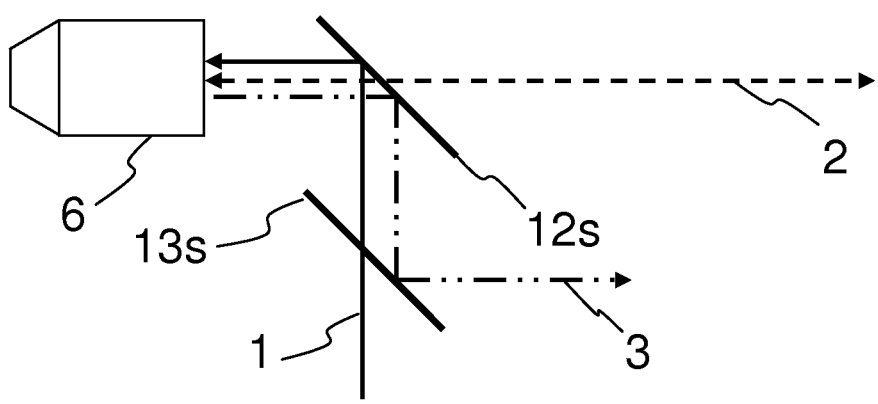

FIG. 27 describes a third embodiment in relation with the spectral distribution of FIG. 24. The filter (12s) allows superimposing the reflected laser excitation beam (1) and the transmitted illumination and viewing beam (2). On the collected scattered beam, the filter (12s) transmits the scattered beam in the viewing band $B_V$ and reflects the scattered beam in the spectral band $B_0$ and in the anti-Stokes Raman scattering band $B_R^{aS}$. The filter (12s) is a high-pass filter whose cut-off wavelength is located between the spectral band $B_0$ and the viewing band $B_V$. The filter (13s) reflects the Raman scattering beam (3) in the anti-Stokes Raman scattering band $B_R^{aS}$ and transmits the Rayleigh scattering beam in the spectral band $B_0$. The filter (13s) is a high-pass or band-pass filter whose cut-off wavelength is located between the anti-Stokes Raman scattering band and the band $B_0$, so as to transmit the band $B_0$ and reflect the anti-Stokes Raman scattering band.

Figure 28:
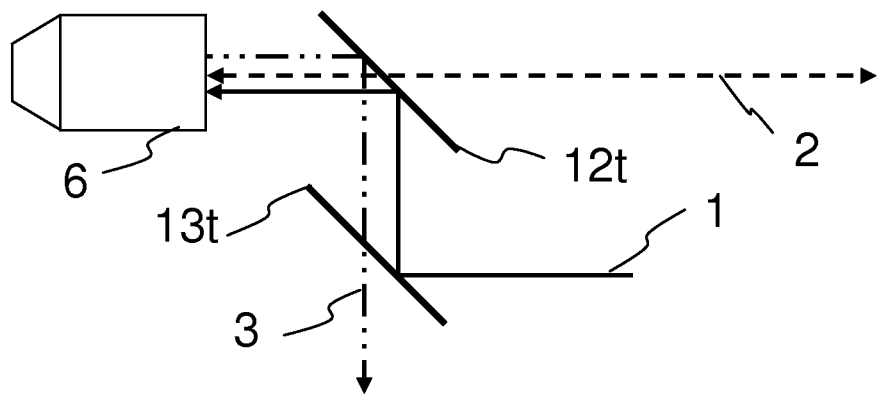

Finally, FIG. 28 describes a fourth embodiment in relation with the spectral distribution of FIG. 24. The filter (12t) allows superimposing the laser excitation beam (1) and the viewing beam (2). On the scattered beam, the filter (12t) reflects the scattered beam in the anti-Stokes Raman scattering band and in the spectral band $B_0$ and transmits the scattered beam in the viewing band $B_V$. The filter (13t) transmits the scattered beam in the anti-Stokes Raman scattering band and reflects the scattered beam in the spectral band $B_0$. The filter (12t) is a high-pass filter having a cut-off wavelength located between the spectral band $B_0$ and the viewing band $B_V$. The filter (12t) thus transmits the viewing band $B_V$ and reflect the spectral band $B_0$ as well as the anti-Stokes Raman scattering band. The filter (13t) is a low-pass or notch filter that transmits the anti-Stokes Raman scattering band, reflects the scattered band in the spectral band $B_0$.

A certain number of embodiments of the invention has been described. However, this description is not limitative and other embodiments of the invention can be contemplated without departing from the scope of the invention (in particular, other types of filters than those of the examples).

In particular, the different embodiment variants of the invention described in relation with FIGS. 2, 6-8, 11-18, 20-23 and 25-28 all relate to a backscattering configuration. However, the same principle also applies to other configurations of Raman scattering (forward scattering or lateral scattering), in which case the means for superimposing the laser excitation beam and the illumination beam are disjoint from the filtering means of the scattering beam. Nevertheless, the principle of using disjoint spectral ranges applies in the same way. The one skilled in the art will thus adapt the device and the method of the invention to the various experimental configurations of Raman spectrometry.

According to still a particularly advantageous embodiment, the same principle is used with several laser excitation wavelengths at the same time and multi-notch filters to separate the various excitation spectral bands, the viewing spectral band and the Raman spectral bands associated respectively to each of the laser excitation wavelengths.

In the various cases of filters used in embodiments in relation with FIGS. 1 to 28, it may be considered that a notch filter performs simultaneously a high-pass filter function and a low-pass filter function. Hence, it is equivalent to replace a high-pass and low-pass filter by a notch filter.

The filters may be made by dielectric stacks or by the VBG (Volume Bragg Grating) technique.

The invention discloses an arrangement of filters with no mobile parts, which allows performing a Raman measurement and viewing the sample, wherein the viewing and the measurement can be simultaneous.

The viewing device of the invention is compact and has overall dimensions equal to half those of a viewing system of the prior art based on a retractable optical component on the optical path.

The device and the method are simple to use, because they require no motor nor mobile parts. The absence of mobile part also makes the device robust.

Finally, the device induces almost no loss on the Raman signal (extremely minimal losses of a few percent).

The extinction rate of the filters may be chosen in such a manner that a very small part of the beam coming from the Rayleigh scattering of the excitation laser beam is transmitted toward the sample viewing system. That way, the viewing system advantageously allows to view simultaneously the sample and the position of the excitation laser beam on the sample. The Rayleigh scattering beam is very attenuated, it does not present a risk of saturation of the viewing sensor, for example a CCD camera.

The possibility to view the sample simultaneously with execution of the Raman measurement makes possible operations based on the processing of the sample image. Therefore, it becomes possible to perform an autofocus adjustment in real time on the sample image during the Raman measurement. Another application made possible by the invention is object monitoring during the Raman measurement or image stabilization (by coupling the device of the invention to a system for moving the object or the sample-carrier). Other automatic applications based, for example, on image processing are also possible in combination with the Raman measurements.

The device of the invention is consisted of fixed elements. This device simultaneously allows viewing a sample and performing a Raman measurement of this sample without inducing high losses of optical intensities.

Advantageously, the optical means of superimposition are merged with the first or the second filtering means, which allows making a more compact and more efficient optical assembly.

The devices of the prior art imply either sequential viewing and measurement, or concomitant viewing and measurement, but with high losses of optical intensity. A device of the prior art based on one or two beam separators (of the separating plate or separating cube type) has an efficiency limited to between 6 and 25%.

The efficiency (in optical transmission) of a device of the invention consisted of two filters is higher than or equal to 90%, or even to 95%. The device of the invention has the advantage to reduce considerably the optical losses, and to allow the measurement of a Raman signal that is always very low.

The invention claimed is:

1. An optical device for Raman spectrometry and for viewing a sample, said device comprising:
    optical superimposition and separation means adapted to be placed on the optical path of an excitation laser beam having a spectral band $B_0$ centered about a wavelength $\lambda_0$ and on the optical path of a viewing beam having a spectral band $B_V$, distinct from the spectral band $B_0$ of the laser and distinct from the spectral band $B_R$ of the Raman scattering beam to be measured, so as to form a combined excitation and viewing incident beam toward the sample, wherein the spectral band $B_0$ of said excitation laser and the spectral band $B_V$ of said viewing beam are defined in wavelength in such a manner that:

$B_V < B_0$;

and the optical superimposition and separation means is adapted to be placed on the path of a collected beam coming from the scattering of the combined excitation and viewing incident beam on the sample, said optical superimposition and separation means comprising:
i. a first filter comprising a dichroic beam splitter for spatially separating said collected beam into a first and a second secondary beam, said first secondary beam comprising one spectral band chosen from the spectral band $B_0$ of the laser, the spectral band $B_V$ of the viewing beam and the spectral band $B_R$ of the Raman scattering beam, and said second secondary beam comprising the two other remaining spectral bands among the spectral band $B_0$ of the laser, the spectral band $B_V$ of the viewing beam and the spectral band $B_R$ of the Raman scattering beam;
ii. a second filter comprising a dichroic beam splitter placed on the path of the second secondary beam for spatially separating said second secondary beam into a first and a second tertiary beam, each respectively comprising one of the two remaining spectral bands among the spectral band $B_0$ of the laser, the spectral band $B_V$ of the viewing beam and the spectral band $B_R$ of the Raman scattering beam, and
a separating plate for directing the viewing beam that goes from the sample to a viewing camera, said viewing camera having a maximum sensitivity about the spectral band $B_V$ in the blue-green-yellow domain of the visible spectrum, and wherein extinction rate for at least one of said first and second filters is chosen in such a manner that a very small part of the Rayleigh scattering beam is transmitted toward the viewing camera so as to allow to view simultaneously the sample and the position of the excitation laser beam on the sample, without saturation of the viewing camera.

2. The device according to claim 1, characterized in that said optical superimposition and separation means are merged with said first filter.

3. The device according to claim 1, characterized in that said optical superimposition and separation means are merged with said second filter.

4. The device according to claim 1, characterized in that said optical superimposition and separation means comprise an optical filter adapted to reflect said excitation laser beam of spectral band $B_0$ and to transmit said viewing beam of spectral band $B_V$.

5. The device according to claim 4, characterized in that said optical filter is chosen among a high-pass, low-pass, band-pass or notch filter.

6. The device according to claim 1, characterized in that said optical superimposition and separation means comprise an optical filter adapted to transmit said excitation laser beam of spectral band $B_0$ and to reflect said viewing beam of spectral band $B_V$.

7. The device according to claim 1, characterized in that said first filter comprises an optical filter adapted to reflect said first secondary beam and to transmit said second secondary beam.

8. The device according to claim 1, characterized in that said first filter comprises an optical filter adapted to transmit said first secondary beam and to reflect said second secondary beam.

9. The device according to claim 1, characterized in that said second filter comprises an optical filter adapted to reflect said first tertiary beam and to transmit said second tertiary beam.

10. The device according to claim 1, characterized in that said second filter comprises an optical filter adapted to transmit said first tertiary beam and to reflect said second tertiary beam.

11. The device according to claim 1, characterized in that the spectral band $B_0$ of the laser, the spectral band $B_V$ of the viewing beam and the spectral band $B_R$ of one or more Stokes lines of the Raman scattering beam are defined in wavelength in such a manner that:

$B_V < B_0 < B_R$.

12. The device according to claim 1, characterized in that the spectral band $B_0$ of the laser, the spectral band $B_V$ of the viewing beam and the spectral band $B_R$ of one or more anti-Stokes lines of the Raman scattering beam are defined in wavelength in such a manner that:

$B_V < B_R < B_0$.

13. The device according to claim 1, characterized in that it further comprises:
at least one excitation laser source adapted to generate an excitation laser beam having a spectral band $B_0$ centered about a wavelength $\lambda_0$,
a viewing light source adapted to generate a viewing beam having spectral band $B_V$ distinct from the spectral band $B_0$ of the laser,
viewing means adapted to detect the collected beam in the spectral band $B_V$,
detection means adapted to detect the Raman scattering beam in the spectral band $B_R$.

14. The device according to claim 1, characterized in that it further comprises autofocus adjustment means.

15. The device according to claim 1, characterized in that it further comprises image stabilization means coupled to means for relative displacement of the object with respect to the laser excitation beam.

16. A method for Raman spectrometry and for viewing a sample comprising the following steps:
superimposing an excitation laser beam having a spectral band $B_0$ centered about a wavelength $\lambda_0$ and a viewing beam having a spectral band $B_V$ distinct from $\lambda_0$ and distinct from the spectral band $B_R$ of the Raman beam to be measured, so as to direct on a sample a combined excitation and illumination beam, wherein the spectral band $B_0$ of said excitation laser and the spectral band $B_V$ of said viewing beam are defined in wavelength in such a manner that:

$B_V < B_0$ and in that the spectral band $B_V$ is in the blue-green-yellow domain of the visible spectrum collecting an optical beam scattered by said sample;
spatially and spectrally separating said collected beam into two secondary beams, the first secondary beam comprising a spectral band chosen among the spectral band $B_0$ of the laser, the spectral band $B_V$ of the viewing beam and the spectral band $B_R$ of the Raman scattering beam, and the second secondary beam comprising the two other remaining spectral bands among the spectral band $B_0$ of the laser, the spectral band $B_V$ of the viewing beam and the spectral band $B_R$ of the Raman scattering beam;

spatially and spectrally separating said second secondary beam into two tertiary beams, each comprising one of the two remaining spectral bands among the spectral band $B_0$ of the laser, the spectral band $B_V$ of the viewing beam and the spectral band $B_R$ of the Raman scattering beam;

directing the viewing beam that goes from the sample to a viewing camera, said viewing camera having a maximum sensitivity about the spectral band $B_V$, simultaneously transmitting a very small part of the Rayleigh scattering beam toward the viewing camera so as to allow to view simultaneously the sample and the position of the excitation laser beam on the sample, without saturating the viewing camera;

detecting the secondary or tertiary collected beam comprising the spectral band $B_R$ of the Raman scattering beam;

detecting the secondary or tertiary collected beam comprising the spectral band $B_V$ of the viewing beam.

17. An optical device for Raman spectrometry and for viewing a sample, the device comprising:
a first filter that:
is positioned in an optical path of an excitation laser beam having a spectral band $B_0$ centered about a wavelength $\lambda_0$ and in an optical path of a viewing beam having a spectral band $B_V$ distinct from the spectral band $B_0$ of the laser and distinct from the spectral band $B_R$ of a Raman scattering beam to be measured with $B_V < B_0$;
combines the excitation laser beam and the viewing beam to form a combined excitation and viewing incident beam illuminating the sample; and
separates a collected beam coming from scattering of the combined excitation and viewing incident beam on the sample into a first and a second secondary beam, the first secondary beam comprising one spectral band chosen from the spectral band $B_0$ of the laser, the spectral band $B_V$ of the viewing beam and the spectral band $B_R$ of the Raman scattering beam, and the second secondary beam comprising the two other remaining spectral bands among the spectral band $B_0$ of the laser, the spectral band $B_V$ of the viewing beam and the spectral band $B_R$ of the Raman scattering beam;

a second filter that:
is positioned in an optical path of the second secondary beam; and
spatially separates the second secondary beam into a first and a second tertiary beam, each respectively comprising one of the two remaining spectral bands among the spectral band $B_0$ of the laser, the spectral band $B_V$ of the viewing beam and the spectral band $B_R$ of the Raman scattering beam; and a viewing camera having a maximum sensitivity about the spectral band $B_V$ in the blue-green-yellow domain of the visible spectrum, wherein an extinction rate of at least one of the first and second filters is chosen such that only a portion of a Rayleigh scattering beam is transmitted toward the viewing camera so as to allow to view simultaneously the sample and the position of the excitation laser beam on the sample, without saturation of the viewing camera.

18. The device of claim 17 further comprising a separating plate positioned to direct the viewing beam from the sample to the viewing camera.

19. The device of claim 17 further comprising an excitation laser having a wavelength in the red or near infrared portion of the electromagnetic spectrum.

20. The device of claim 19 wherein the excitation laser comprises an excitation laser having a nominal wavelength of 680 nm.

* * * * *